United States Patent [19]
Wheeler

[11] Patent Number: 5,007,109
[45] Date of Patent: Apr. 16, 1991

[54] HEAD GEAR HAVING PROTECTIVE LENS

[76] Inventor: Robert L. Wheeler, 823 A E. Gulf Blvd., Indian Rocks Beach, Fla. 33535

[21] Appl. No.: 425,617

[22] Filed: Oct. 20, 1989

[51] Int. Cl.⁵ .............................................. A42B 1/06
[52] U.S. Cl. .............................................. 2/10; 2/12; 351/155
[58] Field of Search ...................... 2/10, 12, 199, 422, 2/427, 9; 351/158, 155

[56] References Cited

U.S. PATENT DOCUMENTS

| | | | |
|---|---|---|---|
| 899,334 | 9/1908 | Seitzman | 2/10 |
| 1,202,307 | 10/1916 | Pachner | 2/10 |
| 1,673,859 | 6/1928 | Wittcoff | 2/10 X |
| 1,729,051 | 9/1929 | Parker | 2/10 |
| 2,328,687 | 9/1943 | Serr | 2/10 |
| 2,619,640 | 12/1952 | Weissberg | 2/10 |
| 2,638,593 | 5/1953 | Eloranta | 2/12 |

FOREIGN PATENT DOCUMENTS

| | | | |
|---|---|---|---|
| 0195128 | 1/1958 | Austria | 2/10 |
| 0202837 | 5/1939 | Switzerland | 2/10 |
| 0107700 | 7/1917 | United Kingdom | 2/10 |

Primary Examiner—Peter Nerbun
Attorney, Agent, or Firm—Joseph C. Mason; Ronald E. Smith

[57] ABSTRACT

A flexible transparent lens that may be darkened to substantially block passage of bright sunlight is releasably or fixedly secured to the underside of a bill of an article of headwear such as a cap. In a first embodiment, buckles are affixed to the upper opposite corners of the lens and complemental snaps are affixed to the opposite rear corners of the bill. The lens follows the contour of the trailing edge of the bill when the snaps and buckles are engaged to one another. The top edge of the lens is spaced forwardly of its bottom edge when the lens is in its bowed configuration so that the bottom edge is closely spaced to the face of the individual wearing the head gear to thereby minimize the amount of sunlight reflected into the individual's eyes from reflective clothing and other sources of reflected sunlight. In another embodiment, the lens is riveted or stapled into position. In all embodiments, the lens may be clear or darkened.

19 Claims, 2 Drawing Sheets

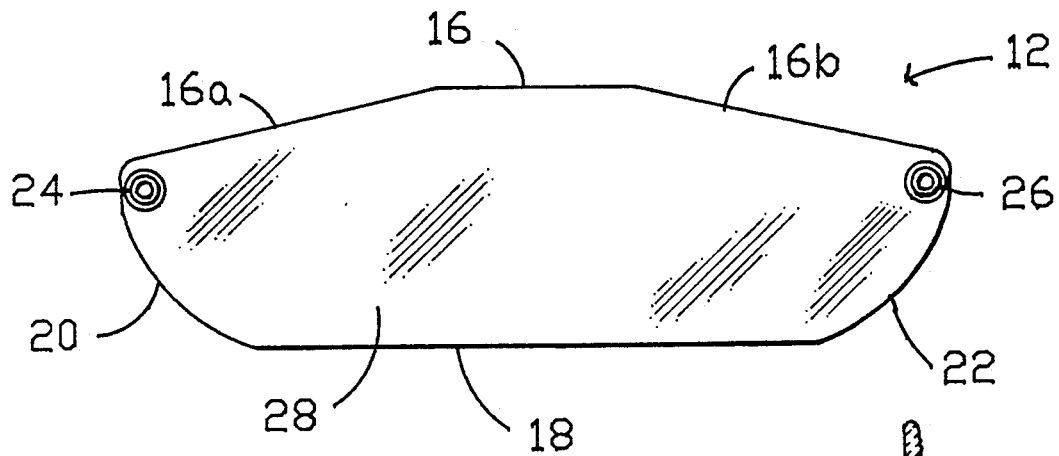
FIG. 4
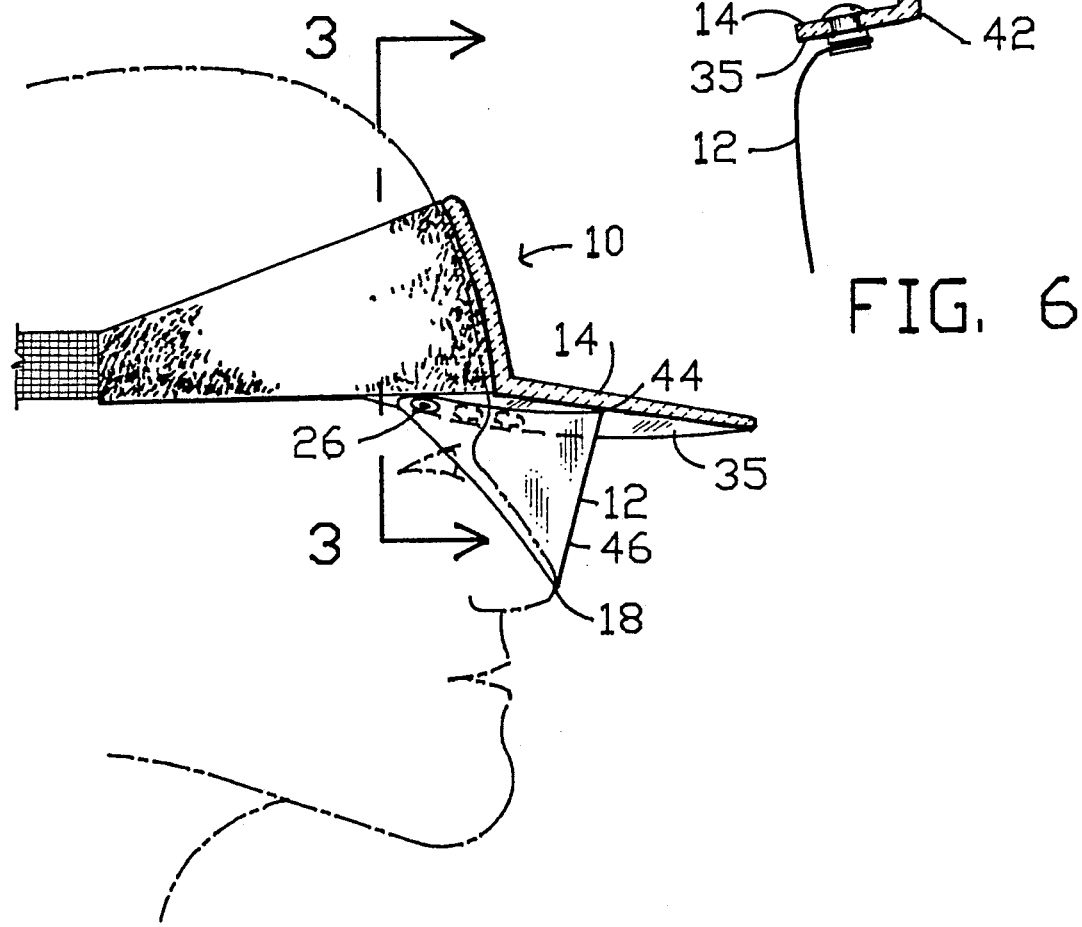
FIG. 6
FIG. 5

HEAD GEAR HAVING PROTECTIVE LENS

TECHNICAL FIELD

This invention relates, generally, to devices that protect one's eyes from bright sunlight. More particularly, it relates to a lens that is removably mounted to the bill of a cap or other article of head wear.

BACKGROUND ART

It is well known that bright sunlight causes discomfort to the human eye. Prolonged exposure to exceptionally bright light, such as sunlight reflected from water, has even been linked to the formation of cataracts.

Accordingly, the wearing of a polarized lens in bright sunlight is advisable. Although sunglasses are commercially available, an individual wearing a white shirt or blouse on a boating trip on a sunny day will still be troubled by light reflecting off the shirt or blouse, which light gets behind the lens of the sunglasses and causes discomfort to the individual.

For those who wear glasses, clip on sunglasses are available but they are even more objectionable than regular sunglasses because the lenses of clip on sunglasses are even further from the eyes of the individual and even more glare gets in.

Inventors have addressed the inadequacy of sunglasses by developing lenses that are attached to the underside of a bill of a cap and which depend therefrom. However, all of the known lenses include bracket members having right angle bends formed therein. Typically, a first part of the bracket is secured to the underside of a bill of a cap, and the second part of the bracket member serves as the mounting plate for a lens. Thus, the lens member is disposed at right angles to the bill throughout its extent. Unfortunately, the bracket members are not only heavy and unsightly, they also restrict the peripheral vision of the individual wearing the cap.

Clearly, the art is well-developed, but just as clearly it has not heretofore attained its highest level of fruition. The devices of the prior art are constructed so that substantial amounts of light still enter the eyes of the individual seeking protection from glare. Significantly, the disclosures of the prior art, taken as a whole, neither teach nor suggest how to construct a device that solves the glare problem.

DISCLOSURE OF INVENTION

An individual wearing a cap or other head wear that includes the teachings or suggestions of this disclosure is completely protected from glare, even if wearing a highly reflective shirt or blouse on a boat, in a desert, or in snow or ice on a sunny day.

First and second buckle members, or other releasable fastening means, are fixedly secured, at laterally opposite sides, to the underside of a bill of a cap, at the rearwardmost extremity thereof. Since the trailing edges of bills, or visors, of caps are arcuate in configuration, the rearwardmost extremities of a bill are the laterally spaced apart back corners thereof.

Mating buckle snaps or other mating releasable fastening means are fixedly secured to laterally opposite sides of a preferably polarized, flexible darkened lens member at the uppermost extremity thereof, i.e., in opposite upper corners thereof. When the buckles releasably engage their associated buckle snaps, the forward surface of each upper corner of the lens and the lower surface of the bill are in very closely spaced, parallel relation to one another, and the top edge of the lens abuts the underside of the bill substantially along its arcuate trailing edge where it is integral to the cap. The main body of the lens is bowed forwardly and substantially follows the contour of the arcuate trailing edge of the bill. The middle of the lens is substantially vertical, but is slightly inclined therefrom. Specifically, the top edge of the lens at its forwardmost point is further forward than is the bottom of the lens at its forwardmost point, relative to the trailing edge of the bill. Thus, ample room is provided to accommodate the nose of the individual wearing the head gear, but the lower edge of the lens touches or nearly touches the chin of the individual, depending upon individual characteristics. Thus, no light reflecting off a white shirt or blouse can get behind the lens.

In an alternative embodiment, the lens is fixedly secured to the head gear by suitable means such as rivets or staples. In another embodiment, the lens is clear.

The primary object of this invention is to provide a sun visor that minimizes the amount of sunlight that can travel around the edges thereof.

Additional objects will become apparent as this description proceeds.

The invention accordingly comprises the features of construction, combination of elements and arrangement of parts that will be exemplified in the construction set forth hereinafter and the scope of the invention will be set forth in the claims.

BRIEF DESCRIPTION OF THE DRAWINGS

For a fuller understanding of the nature and objects of the invention, reference should be made to the following detailed description, taken in connection with the accompanying drawings, in which:

FIG. 4 is a front elevational view of a second embodiment of the novel lens;

FIG. 5 is a sectional view taken along line 5—5 in FIG. 1; and

FIG. 6 is a sectional view showing the novel lens permanently secured to the bill of the cap.

Similar reference numerals refer to similar parts throughout the several views of the drawings.

BEST MODES FOR CARRYING OUT THE INVENTION

Figure 1:
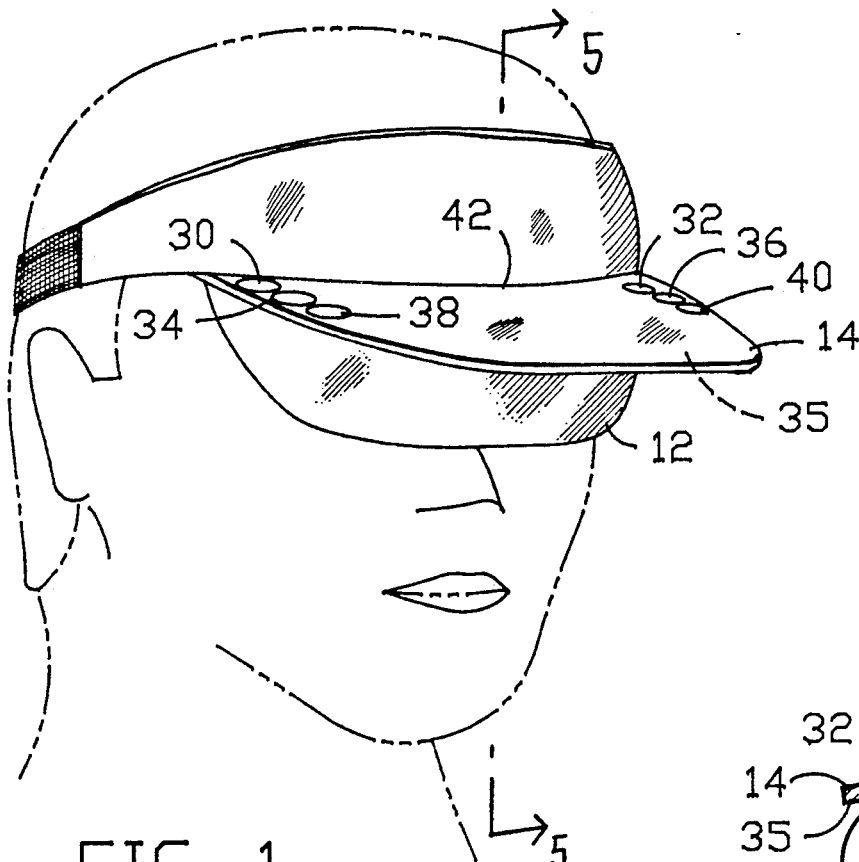
FIG. 1 is a perspective view of an individual wearing an illustrative embodiment of the present invention.

Referring now to the drawings, it will there be seen that an illustrative embodiment of the invention is denoted as a whole by the reference numeral 10.

Although the invention is shown in the environment of a headband or visor, it has equal utility with full caps and any other headwear having a bill.

The inventive structure includes lens 12 and bill 14; the structure of lens 12 will be pointed out first.

Figure 2:
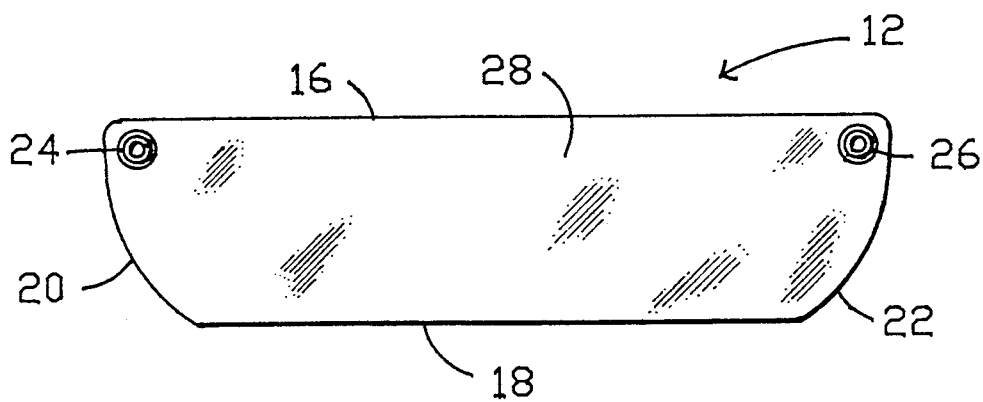
FIG. 2 is a front elevational view of a first embodiment of the novel lens member.

A first embodiment of lens 12 is shown in its flat, unattached configuration in FIG. 2; this particular embodiment has utility in connection with relatively large hats, i.e., caps having bills with a nominal amount of curvature.

The top edge 16 of flexible, preferably polarized, darkened but transparent lens 12 is flat; its bottom edge is also flat and is denoted 18. The arcuate side edges thereof are denoted 20, 22.

Buckle members 24, 26 are fixedly secured to lens 12 in opposite upper corners thereof as shown. Importantly, it should be understood that FIG. 2 is a frontal view of lens 12, i.e., buckles 24, 26 extend from front surface 28 thereof, i.e., out of the paper. The base of each buckle member is double-headed, i.e., of rivet-like construction and impales said lens so that the lens is firmly disposed in sandwiched relation between said double heads to thereby secure said buckles in fixed relation to said lens. The operative, snap-engaging part of each buckle projects out of the paper as aforesaid.

As shown in FIG. 1, a mating buckle snap 30, 32 is similarly fixedly secured to bill 14 so that the operative part of said buckle snap is disposed on the underside 35 of said bill, in the rearwardmost, opposite corners of said bill. Alternatively, additional sets of buckle snaps 34, 36 and 38, 40 may be provided, said additional sets permitting lens 12 to be positioned further from the wearer's face. FIG. 5 shows lens 12 when releasably secured to the middle set of buckle snaps 34, 36, for example.

Figure 3:
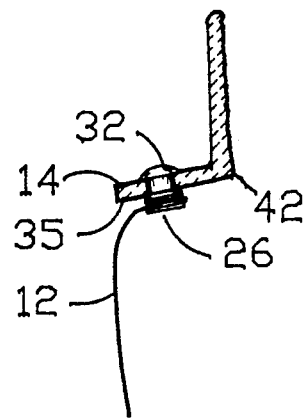
FIG. 3 is a side elevational view of an edge of a bill showing the curvature of the lens in the region of the snaps and buckles.

Accordingly, as is clearly shown in FIG. 3, when buckles 24, 26 respectively engage their associated buckle snap members 30, 32, the forward surface 28 of each upper corner of lens 12 is closely spaced and parallel to the under surface 35 of said bill 30 in the region of the buckles and snaps. The curvature of the bill and this closely spaced parallel relation of the bill and the lens thus bars entry of light at the opposite rearwardmost corners of the bill. Just as importantly, upper edge 16 of lens 12 substantially follows and firmly abuts the trailing arcuate edge 42 of bill 14 along its extent, thereby preventing sunlight from getting past said top edge.

When lens 12 is seen in its bowed or attached configuration, in side elevation or in section as shown in FIG. 5, it is apparent that the middle or forwardmost point 44 of upper edge 16 of lens 12 is spaced forwardly of the middle or forwardmost part 46 of lower edge 18. The bowed lens closely follows the contour of the face, and the bottom edge of the lens is closer to the face than is the top edge. Accordingly, sunlight cannot get past bottom edge 18 of lens 12 even when the individual is wearing reflective clothing.

A second embodiment of lens 12 is shown in FIG. 4 and has increased utility in connection with narrower bills, i.e., bills with increased curvature. It has a flat part 16 in its upper edge that is flanked by downwardly inclined upper edges 16a, 16b; as indicated by the reference numerals, it is similar in all other respects to the lens of FIG. 2.

Lens 12 may also be clear instead of darkened. A clear lens has utility when worn by an individual such as a police officer at a firing range because it keeps powder from the shooter's eyes.

In a final embodiment, shown in FIG. 6, the opposite upper corners of the lens are riveted, stapled or otherwise fixedly secured by unitary fastening members 50, only one of which is shown, to the underside of the bill. The unique curvature of the lens at its opposite, uppermost corners is maintained in this final embodiment when the lens is permanently secured to the bill by said fastening members.

This unique design thus provides the first fully effective lens for shielding the eyes from direct or reflected sunlight. Since the main part of lens 12 is substantially perpendicular to the bill (and to the wearer's line of sight) when the lens is installed and the flexed upper opposite corners thereof are substantially perpendicular to the main body part and since the main part of the lens is bowed so that it generally follows the arcuate trailing edge of the bill, it easily accommodates the nose of the individual wearing the head gear. It also accommodates glasses or spectacles that may be worn by the individual. Moreover, since the lens is canted from the vertical, sloping slightly rearwardly from its top edge to its bottom edge, and closely follows the individual's face along its extent, it provides the maximum protection possible for the effects of reflected sunlight and as such represents the culmination of inventive effort in this field.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A device for shielding the eyes from direct or reflected sunlight, comprising:

a thin flexible lens of flat configuration when in repose;

said lens having a forward surface, a rearward surface, and a predetermined configuration;

a first pair of releasable fastening members being fixedly secured to opposite upper corners of said forward surface of said lens;

each member of said first pair of fastening members having an operative part that projects upwardly from said forward surface;

a headwear member;

a forwardly projecting bill member integral to said headwear member;

said bill member having a top surface and a bottom surface;

said bill member having a leading edge and an arcuate trailing edge that follows the contour of said headwear member;

a second pair of releasable fastening members fixedly secured to said bottom surface of said bill member at opposite ends thereof in closely spaced relation to said trailing edge;

said first and second pair of fastening members being of independent construction relative to one another;

said first and second pair of fastening members being releasably securable to one another;

said lens having a gradual bend formed therein adjacent said respective upper corners of said lens when said first and second independently constructed fastening members are releasably secured to one another, said respective upper corners being in closely spaced, parallel relation to said bill member bottom surface when said first and second independently constructed fastening members are releasably secured to one another.

2. The lens of claim 1, said lens further including a top edge of predetermined contour, and said top edge firmly abutting the arcuate trailing edge of said bill member when said first and second pairs of fastening members are secured to one another so that substantially no light can pass between the bottom surface of said bill member and the top edge of said lens.

3. The lens of claim 2, said lens further including a bottom edge of predetermined contour, and a medial point of said top edge of said lens being spaced forwardly of a medial point of said bottom edge of said lens when said first and second pair of fastening members are secured to one another.

4. The lens of claim 3, wherein said bottom edge of said lens is disposed in closely spaced relation to the face of an individual wearing said headwear member so that light reflected off the clothing of said individual is substantially shielded from the individual's eyes by said lens.

5. The lens of claim 4, wherein said lens is formed of a clear material.

6. The lens of claim 4, where said lens is formed of a darkened material.

7. An article of headwear of the type having a bill comprising:
   a lens members;
   said lens member being of planar structure when in repose and being flexible so that it can be bowed;
   said lens member having a generally rectangular configuration, having top, side and bottom edges of predetermined contour, and having a front surface and a back surface;
   said bill having an arcuate training edge integral to said headwear;
   a first fastening member, of independent construction, being fixedly secured to a first upper corner of said lens member;
   a second fastening member, of independent construction, being fixedly secured to a second upper corner of said lens member, said second upper corner being laterally spaced apart from said first upper corner;
   each of said first and second fastening members having an operative part extending forwardly from the forward surface of said lens member;
   said bill having an upper surface, a lower surface, and an arcuate trailing edge that conforms to the arcuate contour of said article of headwear;
   a third fastening member, of independent construction, being fixedly secured to a lower surface of said bill at a first rear corner of said bill adjacent said trailing edge;
   a forth fastening member, of independent construction, being fixedly secured to a lower surface of said bill at a second rear corner of said bill adjacent said trailing edge;
   said first and second rear corners of said bill being laterally spaced apart from one another;
   a first gradual bend being formed in said lens adjacent said first upper corner of said lens member when said first and third fastening members of independent construction are releasably engaged to one another, said first upper corner of said lens member being disposed in closely spaced, parallel relation to the lower surface of said bill, as a result of said first gradual bend, when said first and third fastening members are so engaged;
   a second gradual bend being formed in said lens adjacent said second upper corner of said lens member when said second and fourth fastening members are releasably engaged to one another, said second upper corner of said lens member being disposed in closely spaced, parallel relation to the lower surface of said bill, as a result of said second gradual bend, when said first and third fastening members are so engaged;
   said lens member having a main part disposed substantially perpendicular to said bill;
   said lens member having a preselected lateral extent greater than the lateral extent of said headwear when said lens member is in a flat configuration; and
   said lens member being bowed forwardly when said fastening members are engaged to one another such that the curvature of said lens member main part substantially follows the curvature of said arcuate trailing edge of said bill.

8. The article of claim 7, wherein the top edge of said lens member is spaced forwardly of the bottom edge thereof when said fastening members are engaged to one another, relative to said arcuate trailing edge of said bill.

9. The article of claim 8, wherein said top edge is flat along its extent.

10. The article of claim 8, wherein said top edge has a flat medial part and downwardly inclined parts that flank said medial part.

11. The lens member of claim 7, wherein said lens is formed of a transparent material.

12. The lens member of claim 7, wherein said lens is formed of a darkened material.

13. A device attached to an article of headgear of the type having a bill, comprising:
   a flexible lens member;
   said lens member having a forward surface, a rearward surface, and a generally rectangular configuration;
   said lens member having opposite, laterally spaced upper corners;
   said upper corners being disposed in substantially parallel and closely spaced relation to an underside of said bill;
   said bill having an arcuate leading edge, an arcuate trailing edge, and having opposite, laterally spaced corners where said leading and trailing edges converge;
   said lens member having a main body part disposed substantially orthogonally to said bill;
   said main body part of said lens member being bowed so that it generally follows the arcuate contour of said headgear where said bill projects therefrom;
   first and second fastening members being fixedly secured to respective upper corners of said forward surface of said lens member and third and fourth fastening members being fixedly secured to respective lower corners of said bill;
   each of said first, second, third and fourth fastening members being formed separately relative to one another;
   said first and third fastening members being releasably engageable to one another;
   a first gradual bend being formed in said lens member adjacent a first upper corner thereof when said first and third fastening members are releasably engaged to one another, said first upper corner of said lens being disposed in closely spaced, parallel relation to said bill underside when said first and second fastening members are so engaged;

said second and fourth fastening members being releasably engagable to one another;

a second gradual bend being formed in said lens member adjacent a second upper corner thereof when said second and fourth fastening members are releasably engaged to one another, said second upper corner of said lens being disposed in closely spaced parallel relation to said bill underside when said second and fourth fastening members are so engaged.

14. The device of claim 13, wherein said means for fixedly securing said lens member is rivets.

15. The device of claim 13, wherein said means for fixedly securing said lens member is staples.

16. The device of claim 13, wherein the substantially entire extent of an upper edge of said lens member is spaced outwardly of substantially the entire extent of a bottom edge thereof relative to the face of an individual wearing said headgear.

17. The device of claim 13, wherein said lens member is transparent.

18. The device of claim 13, wherein said lens member is darkened.

19. A device for shielding the eyes from direct or reflected sunlight comprising:

a thin flexible lens of flat configuration when in repose;

said lens having a forward surface, a rearward surface, and a predetermined configuration;

a headwear member;

a forwardly projecting bill member integral to said headwear member;

said bill member having a top surface and a bottom surface;

said bill member having a leading edge and an arcuate trailing edge that follows the contour of said headwear member;

said bill member having a pair of laterally spaced corners where said leading edge and said trailing edge meet;

said lens having a pair of laterally spaced corners adjacent an upper edge of said lens;

a pair of laterally spaced fastening members, of unitary construction, being disposed in permanent interconnecting relation to the respective corners of said lens and the respective corners of said bill member;

said lens having a gradual bend formed therein adjacent each of said corners of said lens when said lens is permanently interconnected to said bill member by said fastening members of unitary construction; and said lens corners being in closely spaced, parallel relation to said bottom surface of said bill member when said lens is permanently interconnected to said bill member by said fastening members.

* * * * *